(12) United States Patent  
Hartman

(10) Patent No.: US 6,907,677 B1
(45) Date of Patent: Jun. 21, 2005

(54) STABLE LVDT EXTENSOMETER

(75) Inventor: George A. Hartman, Waynesville, OH (US)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 0 days.

(21) Appl. No.: 10/346,817

(22) Filed: Jan. 18, 2003

Related U.S. Application Data

(60) Provisional application No. 60/349,768, filed on Jan. 18, 2002.

(51) Int. Cl.[7] .................................................. G01B 7/16
(52) U.S. Cl. .......................................... 33/787; 33/789
(58) Field of Search ..................... 33/787, 788, 789, 33/790, 783, 784, 501.06, 501.5; 73/782, 799, 780

(56) References Cited

U.S. PATENT DOCUMENTS

| | | | | | |
|---|---|---|---|---|---|
| 2,077,598 | A | * | 4/1937 | Von Heydekampf | 33/790 |
| 2,085,687 | A | * | 6/1937 | Peters | 33/790 |
| 2,292,326 | A | * | 8/1942 | Lewis | 33/790 |
| 3,158,939 | A | * | 12/1964 | Brooks, Jr. | 33/787 |
| 3,559,467 | A | * | 2/1971 | Gurol et al. | 73/782 |
| 3,602,866 | A | * | 8/1971 | Saxl | 338/5 |
| 4,251,918 | A | * | 2/1981 | Duggan | 33/790 |
| 4,481,826 | A | * | 11/1984 | Ingraffea | 73/799 |
| 4,881,324 | A | * | 11/1989 | Khinchuk | 33/555.1 |
| 5,537,754 | A | * | 7/1996 | Bachmann et al. | 33/787 |
| 5,819,428 | A | * | 10/1998 | Meyer | 33/787 |
| 5,861,559 | A | * | 1/1999 | Solomon et al. | 73/799 |

FOREIGN PATENT DOCUMENTS

| | | | | | |
|---|---|---|---|---|---|
| JP | 07092068 | A | * | 4/1995 | G01N/3/34 |
| JP | 11083419 | A | * | 3/1999 | G01B/7/16 |
| WO | WO 9427112 | A1 | * | 11/1994 | G01B/7/16 |

* cited by examiner

Primary Examiner—R. Alexander Smith
(74) Attorney, Agent, or Firm—AFMCLO/JAZ; Fredric L. Sinder

(57) ABSTRACT

A new extensometer is disclosed that avoids prior art problems of drift and other problems from variations in temperature, humidity and other environmental factors. Two primary extensometer body parts each hold at one end specimen contact rods and at their other ends a displacement measuring sensor, preferably a linear variable differential transformer. A thin hinge area connects the two body parts into a single piece monolithic construction so that relative movement between the two body parts is restricted to a single rotational degree of freedom.

4 Claims, 2 Drawing Sheets

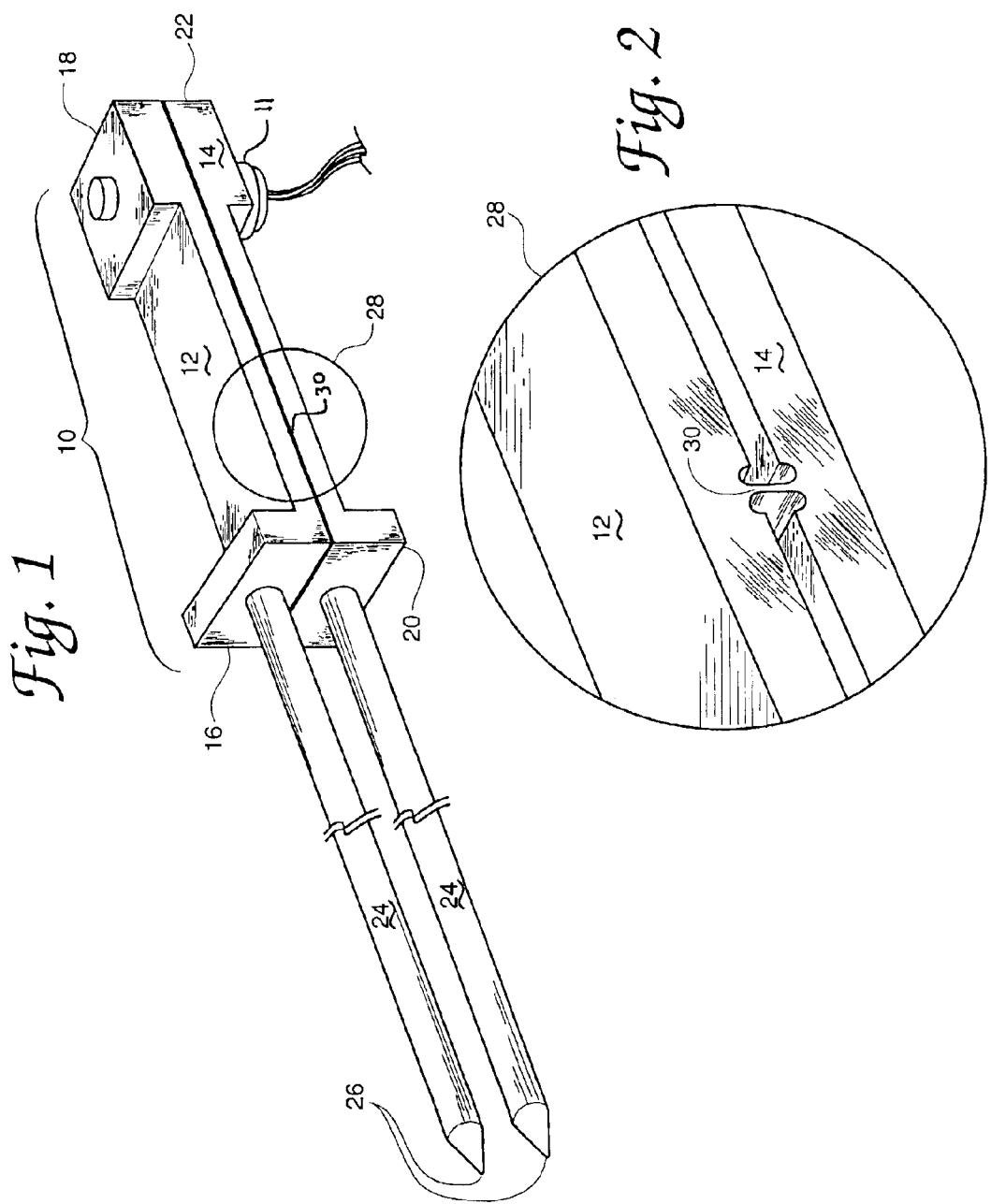

STABLE LVDT EXTENSOMETER

This application claims priority under 35 U.S.C. § 119(e) from U.S. provisional application No. 60/349,768, filed Jan. 18, 2002, by applicant George A. Hartman, titled "Stable LVDT Extensometer". The invention description contained in that provisional application is incorporated by reference into this description.

RIGHTS OF THE GOVERNMENT

The invention described herein may be manufactured and used by or for the Government of the United States for all governmental purposes without the payment of any royalty.

BACKGROUND OF THE INVENTION

The present invention relates generally to extensometers, and more specifically to high temperature extensometers used, for example, for measuring high temperature creep of unidirectional composite materials.

Extensometers measure strain on a test specimen subjected to tensile, compression, fatigue or creep tests. Extensometers generally have a pair of arms connected together with some sort of spacing mechanism. The arms are coupled to move with the specimen during testing. A measuring device measures a change in distance between the arms in order to measure elongation or compression of the test specimen.

An example improvement to prior art extensometers may be found in U.S. Pat. No. 5,600,895 to Meyer et al. An example improvement specifically directed to high temperature testing may be found in U.S. Pat. No. 4,884,456 to Meline et al.

Most extensometers used for creep testing use strain gauges. Variations in strain readings, primarily drift, using such strain gauges have been a problem. Creep testing is typically performed over long time periods. Particularly at the low strain rates used for many composite creep tests, the strain readings over time are affected by many environmental factors. Electrical interference from the test system itself can cause a high frequency noise band of up to ±150 microstrain. Although electrical noise is not the source of the gradual changes in strain typically present in such creep tests, that noise is an indication of the limited range of strain gauge type extensometers. Such electrical noise may be reduced by additional filters or shielding.

The major source of strain variations over time during creep tests has been discovered to be the sensitivity of strain gauge type extensometers to changes in relative humidity. During a series of test at room temperature with the extensometer rods held in a fixed position as the relative humidity changed over time, the strain reading from the extensometer also changed up to ±150 microstrain. Even worse, in room air the changes in strain readings lagged behind humidity changes by 4 to 18 hours depending on the rate at which the humidity level changed. Placing an extensometer inside a vacuum chamber showed a further example of the effect of humidity. As air was evacuated from the chamber, the strain reading steadily decreased despite that the extensometer rods were held fixed. When room air was reintroduced into the chamber, the strain readings gradually returned to pretest levels.

The cause of the variation in strain readings was not determined, but may be due to the effects of moisture content on the strain gauges mounted on the extensometer or on the epoxy used to attach the strain gauges.

To minimize the effects of humidity on strain gauge readings, either the environment will have to be better controlled or another type of strain reading device not affected by humidity changes will have to be used. Attempting to better control the environment will be both expensive and introduce variations on its own, partly because the environment will be differently controlled at different test sites and at different times. A different type of strain reading device will more likely produce uniform, reproducible and comparable results at different times and locations.

Thus it is seen that there is a need for extensometers, particularly extensometers used in high temperature creep testing, that are nearly unaffected by changes in humidity, temperature and other environmental factors.

It is, therefore, a principal object of the present invention to provide an extensometer that is nearly unaffected by changes in humidity and other environmental factors.

It is an advantage of the present invention that it can be calibrated to be more sensitive to displacement than prior art extensometers while maintaining a more stable output.

It is a feature of the present invention that it is made using only one piece, providing the advantage of avoiding the errors in small-scale measurements from gaps at the interfaces between pieces.

It is another feature of the present invention that its physical geometry is such that all but one of the six degrees of freedom of movement are constrained, providing the advantage that only what is being measured can move.

It is another advantage of the present invention that its solid flexure configuration avoids hysteresis and non-linearity associated with moving mechanical connections.

These and other objects, features and advantages of the present invention will become apparent as the description of a representative embodiment proceeds.

SUMMARY OF THE INVENTION

In accordance with the foregoing principles and objects of the present invention, a novel extensometer is described. The unique discovery of the present invention is a single piece or monolithic extensometer that results in a very stable extensometer mostly unaffected by environmental changes over time and particularly useful for high temperature creep testing. The extensometer has two primary body parts, each body part for holding one of a pair of specimen contact rods, connected only by a thin hinge area so that relative movement of the two body parts is constrained to a single degree of freedom, rotation about a long axis of the thin hinge areas. The extensometer body is preferably made of a material having a near-zero coefficient of thermal expansion, such as CARPENTER INVAR 36. The sensor for measuring the rotation is preferably a linear variable differential transformer (LVDT) that measures displacement by detecting variations in an electric field as a copper rod moves inside the field. An LVDT has been shown to be inherently unaffected, or less effected, by humidity changes and its electrical noise level has been discovered to be as low as that obtained using strain gauge type extensomers. The LVDT sensor is preferably hermetically sealed.

Accordingly, the present invention is directed to an extensometer body, comprising first body part having a long axis and a short axis, the short axis transverse to the long axis, the first body part having at a first end of its long axis an opening configured for attaching a first end of a linear variable differential transformer and at a second end of its long axis an opening configured for attaching a first specimen contact rod; a second body part having a long axis parallel to the first body part long axis and a short axis parallel to the first body part short axis, the second body part having at a first end of its long axis an opening configured for attaching a second end of a linear variable differential transformer and at a second end of its long axis an opening configured for attaching a second specimen contact rod; and, a thin flexure body part positioned between the first and second body parts having a long axis parallel to short axes of the first and second body parts and bridging the first and second body parts together into a single piece capable of relative movement between the first and second body parts generally only in rotation about the long axis of the thin flexure body part.

The invention is further directed to an extensometer, comprising an extensometer body as described in the preceding paragraph; a linear variable differential transformer attached at the first ends of the first and second body parts; and, first and second specimen contact rods attached at respective first ends of the specimen contact rods to respective second ends of the first and second body parts.

The invention is still further directed to a method for measuring expansion and contraction of a test specimen, comprising the steps of providing an extensometer, the extensometer including an extensometer body including a first body part having a long axis and a short axis, the short axis transverse to the long axis, the first body part having at a first end of its long axis an opening configured for attaching a first end of a linear variable differential transformer and at a second end of its long axis an opening configured for attaching a first specimen contact rod; a second body part having a long axis parallel to the first body part long axis and a short axis parallel to the first body part short axis, the second body part having at a first end of its long axis an opening configured for attaching a second end of a linear variable differential transformer and at a second end of its long axis an opening configured for attaching a second specimen contact rod; and, a thin flexure body part positioned between the first and second body parts having a long axis parallel to short axes of the first and second body parts and bridging the first and second body parts together into a single piece capable of relative movement between the first and second body parts generally only in rotation about the long axis of the thin flexure body part; attaching a displacement measuring sensor to the first ends of the first and second body parts; attaching first and second specimen contact rods to first ends of the specimen contact rods to respective second ends of the first and second body parts; contacting the specimen contact rods to a test specimen; and measuring movement along the test specimen by relative movement of the specimen contact rods measured by movement at the displacement measuring sensor. The displacement measuring sensor may be a linear variable differential transformer.

BRIEF DESCRIPTION OF THE DRAWINGS

The present invention will be more clearly understood from a reading of the following detailed description in conjunction with the accompanying drawings wherein:

FIG. 1 is a representational view of an LVDT extensometer according to the teachings of the present invention showing a perspective view of an extensometer body, an LVDT sensor and a pair of attached specimen contact rods for contacting a specimen to be tested;

FIG. 2 is an enlarged view of the flexure portion of the LVDT extensometer of FIG. 1 showing details of the narrow hinge-like configuration that is a key element of the invention; and, FIG. 3 is another perspective view of an LVDT extensometer according to the teachings of the present invention showing a perspective view of slightly greater detail of an example configuration and openings for attaching and mounting specimen contact rods and an LVDT sensor.

DETAILED DESCRIPTION

Figure 3:
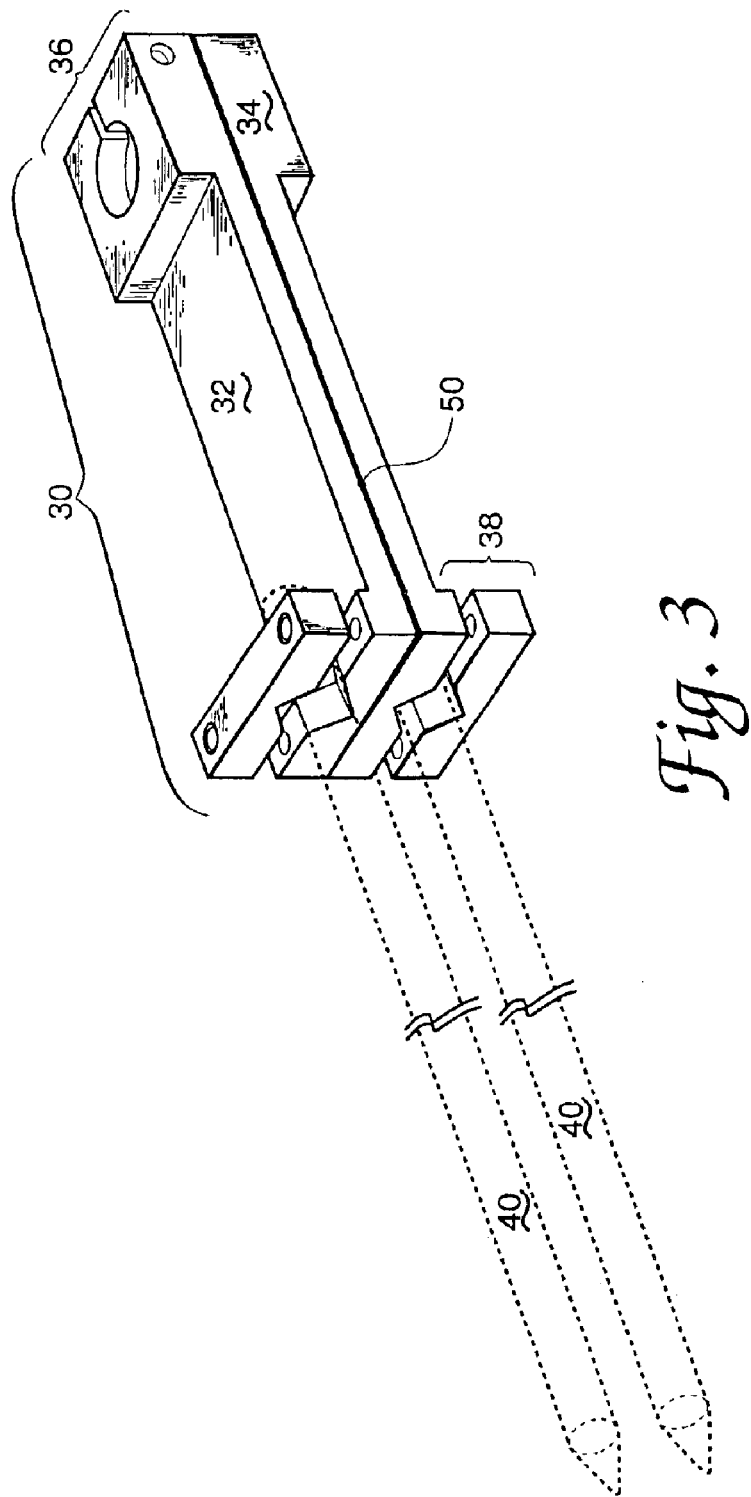

Referring now to FIG. 1 of the drawings, there is shown a representational view of an LVDT extensometer according to the teachings of the present invention showing a perspective view of an extensometer body 10, an LVDT sensor 11 and a pair of attached specimen contact rods 24 for contacting a specimen to be tested. Extensometer body 10 comprises a first body part 12 and a second body part 14. First body part 12 and second body part 14 each have a long axis at which respective ends 18 and 22 extensometer body 10 is configured for mounting LVDT sensor 11. Similarly, first and second body parts 12 and 14 are each configured at respective other ends 16 and 20 of each long axis for attaching or mounting specimen contract rods 24. Each specimen contact rod 24 includes a tip 26 for contacting a specimen to be tested. Contact rods 24 will typically be made of quartz or other material able to withstand high temperatures. Contact rods 14 are long because in typical use they extend inside a heating chamber to contact a specimen being tested at higher temperatures than extensometer body 10 and LVDT sensor 11 can withstand.

FIG. 2 is an enlarged view of a flexure body part 30 of the LVDT extensometer of FIG. 1 showing details of the narrow hinge-like configuration that is a key element of the invention. Examination of flexure body part 30 shows that in this preferred configuration it constrains relative movement of first body part 12 and second body part 14 to a single degree of freedom, rotation about a long axis of flexure body part 30 transverse to the long axes of first and second body parts 12 and 14. The width of flexure body part 30 along its long axis restricts rotation about an axis orthogonal to the long axes of first and second body parts 12 and 14 and flexure body 30; restricts relative movement of first and second body parts 12 and 14 along their mutual long axes; and, restricts relative movement of first and second body parts 12 and 14 along the short axis of flexure body part 30. The height and cross-sectional width of flexure body part 30 restricts relative movement up and down the just described orthogonal axis.

Flexure body part 30 is also sized and shaped that, while minimizing motion of specimen contact rod tips except in the desired single degree of freedom, also producing low enough stresses in the solid-state flexure to provide a reasonable service life.

FIG. 3 is another perspective view of an LVDT extensometer body 30 according to the teachings of the present invention. Example ends 36 and 38 of first and second body parts 32 and 34, respectively, show slightly greater details of an example configuration and openings, both bolt and mounting, for attaching and mounting specimen contact rods 40 and an LVDT or other displacement measuring sensor.

LVDT sensors are commonly available. LVDT sensors available from Schaevitz Sensors in Hampton, Va. have worked well. Performance of the LVDT extensometer is improved by hermetically sealing the LVDT extensometer. Carpenter INVAR 36, well-known for its near zero coefficient of thermal expansion, has worked well for making the extensometer bodies.

The disclosed extensometer successfully demonstrates the advantages of a single piece or monolithic configuration for an extensometer, combined with the advantages of using a LVDT sensor and a low thermal coefficient of expansion material. Although the disclosed invention is specialized, its teachings will find application in other areas where prior art configurations comprise multipiece mechanisms with undesirable flexing and other relative movement between parts.

Those with skill in the art of the invention will readily see that the described extensometer body can be made in a variety of other configurations and still demonstrate the advantages of its monolithic construction. For example, while an LVDT is preferred as a displacement measuring sensors, other sensors may also be used, both now known and as may be discovered in the future. Also, the specimen contact rods are described as rods, but are understood to include any configuration, whether or not rod shaped, for attaching to a test specimen, the same as if the term "member" were used instead of "rod," a goal of patent claim drafting being the use of readily understood terms in place of terms so general it is difficult to easily grasp the intended meaning of the claims. It is understood, therefore, that other modifications to the invention may be made, as might occur to one with skill in the field of this invention, within the scope of the claims. All embodiments contemplated have not been shown in complete detail. Other embodiments may be developed without departing from the spirit of this invention or from the scope of the claims.

I claim:

1. An extensometer body, comprising:
   (a) a first body part having a long axis, and a short axis, the short axis transverse to the long axis, the first body part having at a first end of its long axis an opening configured for attaching a first end of a linear variable differential transformer and at a second end of its long axis an opening configured for attaching a first specimen contact rod;
   (b) a second body part having a long axis parallel to the first body part long axis and a short axis parallel to the first body part short axis, the second body part having at a first end of its long axis an opening configured for attaching a second end of the linear variable differential transformer and at a second end of its long axis an opening configured for attaching a second specimen contact rod;
   (c) a thin flexure body part positioned between the first and second body parts having a long axis parallel to the short axis of the first and second body parts and bridging the first and second body parts together into a single piece capable of relative movement between the first and second body parts generally only in rotation about the long axis of the thin flexure body part; and,
   (d) wherein the thin flexure body part is longitudinally spaced between the first end of the long axis of the first body part and the second end of the long axis of the first body part, and wherein the thin flexure body part is also longitudinally spaced between the first end of the long axis of the second body part and the second end of the long axis of the second body part.

2. An extensometer, comprising:
   (a) an extensometer body, including:
      (i) a first body part having a long axis and a short axis, the short axis transverse to the long axis and the long axis having a first end and a second end;
      (ii) a second body part having a long axis parallel to the first body part long axis and a short axis parallel to the first body part short axis, the long axis having a first end and a second end;
      (iii) a thin flexure body part positioned between the first and second body parts having a long axis parallel to the short axes of the first and second body parts and bridging the first and second body parts together into a single piece capable of relative movement between the first and second body parts generally only in rotation about the long axis of the thin flexure body part; and,
      (iv) wherein the thin flexure body part is longitudinally spaced between the first end of the long axis of the first body part and the second end of the long axis of the first body part, and wherein the thin flexure body part is also longitudinally spaced between the first end of the long axis of the second body part and the second end of the long axis of the second body part;
   (b) a linear variable differential transformer having two ends attached at its two ends to the respective first ends of the first and second body parts; and,
   (c) first and second specimen contact rods attached at respective first ends of the specimen contact rods to respective second ends of the first and second body parts.

3. A method for measuring expansion and contraction of a test specimen, comprising the steps of:
   (a) providing an extensometer, the extensometer including an extensometer body including:
      (i) a first body part having a long axis and a short axis, the short axis transverse to the long axis and the long axis having a first end and a second end;
      (ii) a second body part having a long axis parallel to the first body part long axis and a short axis parallel to the first body part short axis, the long axis having a first end and a second end;
      (iii) a thin flexure body part positioned between the first and second body parts having a long axis parallel to short axes of the first and second body parts and bridging the first and second body parts together into a single piece capable of relative movement between the first and second body parts generally only in rotation about the long axis of the thin flexure body part; and
      (iv) wherein the thin flexure body part is longitudinally spaced between the first end of the long axis of the first body part and the second end of the long axis of the first body part, and wherein the thin flexure body part is also longitudinally spaced between the first end of the long axis of the second body part and the second end of the long axis of the second body part;
   (b) attaching a displacement measuring sensor having two ends to the respective first ends of the first and second body parts;
   (c) attaching first and second specimen contact rods having respective first ends to the respective second ends of the first and second body parts;
   (d) contacting the specimen contact rods to a test specimen;
   (e) measuring movement along the test specimen by relative movement of the specimen contact rods measured by movement at the displacement measuring sensor.

4. The method for measuring expansion and contraction of a test specimen as described in claim 3, wherein the displacement measuring sensor is a linear variable differential transformer.

* * * * *